United States Patent
Furuta et al.

(10) Patent No.: US 10,365,033 B2
(45) Date of Patent: Jul. 30, 2019

(54) REFRIGERATOR WITH ADVICE GENERATING UNIT

(71) Applicant: Toshiba Lifestyle Products & Services Corporation, Tokyo (JP)

(72) Inventors: Kazuhiro Furuta, Tokyo (JP); Yuuki Marutani, Tokyo (JP); Takuya Mashimo, Tokyo (JP)

(73) Assignee: Toshiba Lifestyle Products & Services Corporation, Tokyo (JP)

( * ) Notice: Subject to any disclaimer, the term of this patent is extended or adjusted under 35 U.S.C. 154(b) by 662 days.

(21) Appl. No.: 14/663,353

(22) Filed: Mar. 19, 2015

(65) Prior Publication Data
US 2015/0260449 A1  Sep. 17, 2015

Related U.S. Application Data

(63) Continuation of application No. PCT/JP2013/073800, filed on Sep. 4, 2013.

(30) Foreign Application Priority Data

Sep. 25, 2012 (JP) ................................ 2012-210849

(51) Int. Cl.
*G09B 19/00* (2006.01)
*F25D 29/00* (2006.01)
(Continued)

(52) U.S. Cl.
CPC .......... *F25D 29/00* (2013.01); *G09B 19/0092* (2013.01); *F25D 2400/361* (2013.01);
(Continued)

(58) Field of Classification Search
CPC ............. G09B 19/0092; F25D 2700/02; F25D 2700/04; F25D 2700/06
See application file for complete search history.

(56) References Cited

U.S. PATENT DOCUMENTS

| | | | | |
|---|---|---|---|---|
| 4,241,337 A | * | 12/1980 | Prada | .................... F25D 29/008 200/61.69 |
| 2004/0035123 A1 | * | 2/2004 | Kim | ........................ F25D 29/00 62/127 |

(Continued)

FOREIGN PATENT DOCUMENTS

| CN | 101071014 | 11/2007 |
|---|---|---|
| CN | 101180508 A | 5/2008 |

(Continued)

OTHER PUBLICATIONS

Chinese Office Action issued in CN 201380049761.X dated Apr. 12, 2017.

(Continued)

*Primary Examiner* — Edward F Landrum
*Assistant Examiner* — Daniel C Comings
(74) *Attorney, Agent, or Firm* — DLA Piper LLP US

(57) ABSTRACT

A refrigerator includes a biological information obtaining unit for obtaining biological information of a person upon detection of the person in the vicinity of the refrigerator. The refrigerator further includes an advice generating portion for generating advice about health care based on analysis of the biological information and a display configured to display the advice in response to a user request.

16 Claims, 8 Drawing Sheets

(51) Int. Cl.
G06Q 50/22 (2018.01)
G06Q 10/00 (2012.01)
(52) U.S. Cl.
CPC ...... F25D 2500/06 (2013.01); F25D 2700/02 (2013.01); F25D 2700/04 (2013.01); F25D 2700/06 (2013.01); G06Q 10/00 (2013.01); G06Q 50/22 (2013.01)

(56) References Cited

U.S. PATENT DOCUMENTS

| | | | |
|---|---|---|---|
| 2005/0240444 A1* | 10/2005 | Wooten | G06F 19/3481 705/3 |
| 2006/0217600 A1 | 9/2006 | Lee et al. | |
| 2006/0224050 A1 | 10/2006 | Lee et al. | |
| 2006/0287883 A1* | 12/2006 | Turgiss | G06F 19/3418 705/2 |
| 2007/0150381 A1* | 6/2007 | Pippia | F25D 29/00 705/28 |
| 2008/0052001 A1* | 2/2008 | Bodin | G06F 19/3475 702/1 |
| 2008/0195944 A1 | 8/2008 | Lee et al. | |
| 2008/0250797 A1* | 10/2008 | Rozendaal | F25D 29/00 62/127 |
| 2011/0021140 A1 | 1/2011 | Binier | |
| 2011/0257496 A1* | 10/2011 | Terashima | A61B 5/1486 600/347 |
| 2012/0166210 A1 | 6/2012 | Langcaon et al. | |
| 2012/0180507 A1* | 7/2012 | Leebow | G06F 1/1632 62/129 |

FOREIGN PATENT DOCUMENTS

| | | |
|---|---|---|
| CN | 100394131 C | 6/2008 |
| CN | 101210758 | 7/2008 |
| CN | 102645083 A | 8/2012 |
| JP | 2003-038494 | 2/2003 |
| JP | 2003-235829 | 8/2003 |
| JP | 2004-164442 | 6/2004 |
| JP | 2005-241215 | 9/2005 |
| KR | 2006-0117703 | 11/2006 |
| KR | 2006-0117718 | 11/2006 |
| KR | 20060117718 | 11/2006 |
| KR | 20060134522 | 12/2006 |
| WO | WO 2012/011919 | 1/2012 |

OTHER PUBLICATIONS

Korean Office Action (with English Translation) issued in KR 10-2006-7032020 dated Feb. 6, 2017.
English Language Abstract and Translation of JP 2003-038494 published Feb. 12, 2003.
English Language Abstract and Translation of KR 2004-0017978 published Mar. 2, 2004.
English Language Abstract and Translation of KR 2004-0082804 published Sep. 3, 2004.
English Language Abstract and Translation of KR 2006-0117703 published Nov. 17, 2006.
Notification of Reasons for Refusal (with English Translation) issued in JP 2012-210849 dated Nov. 22, 2016.
Notification of Opinion on Examination (with English Translation) issued TW 102133080 dated Oct. 28, 2016.
Supplementary European Search Report issued in EP 13842804.0 dated Nov. 22, 2016.
English Language Abstract and Translation of KR 2006-0117718 published Nov. 17, 2006.
English Language Abstract and Translation of JP 2003-235829 published Aug. 26, 2003.
Notification of Refusal of Patent (with English Translation) issued in Korean Application No. 10-2015-7003044 dated Oct. 18, 2016.
Notification of Refusal of Patent (with English Translation) issued in Korean Application No. 10-2015-7003044 dated Sep. 5, 2016.
Second Notification of Opinion on Examination (with English Translation) issued in CN 20130049761.X dated Jun. 29, 2016.
Taiwan Office Action issued in TW 10520221200 dated Feb. 24, 2016 with English Language Translation.
English language Abstract and machine Translation of CN 101071014 published on Nov. 14, 2007.
English language Abstract and machine Translation of CN 101210758 published on Jul. 2, 2008.
English language Abstract and machine Translation of KR 20060117718 published on Nov. 17, 2006.
English language Abstract and machine Translation of KR 20060134522 published on Dec. 28, 2006.
International Search Report issued in PCT/JP2013/073800 dated Nov. 26, 2013.
Written Opinion issued in PCT/JP2013/073800 dated Nov. 26, 2013.
English language abstract and machine translation of JP 2004-164442 published on Jun. 10, 2004.
English language abstract and machine translation of JP 2005-241215 published on Sep. 8, 2005.
Chinese Office Action issued in CN 201380049761.X dated Dec. 16, 2015 with English language translation.
English language abstract and machine translation of CN 102645083 A published on Aug. 22, 2012.
English language abstract of CN 100394131 C published on Jun. 11, 2008.
English language abstract and machine translation of CN 101180508 A published on May 14, 2008.
Japanese Office Action issued in JP 2012-210849 dated Jun. 7, 2016 with English language translation.
Korean Office Action issued in KR 10-2015 dated Feb. 29, 2016.
European Office Action issued in EP Application No. 13 542 804.0 dated May 24, 2019.

* cited by examiner

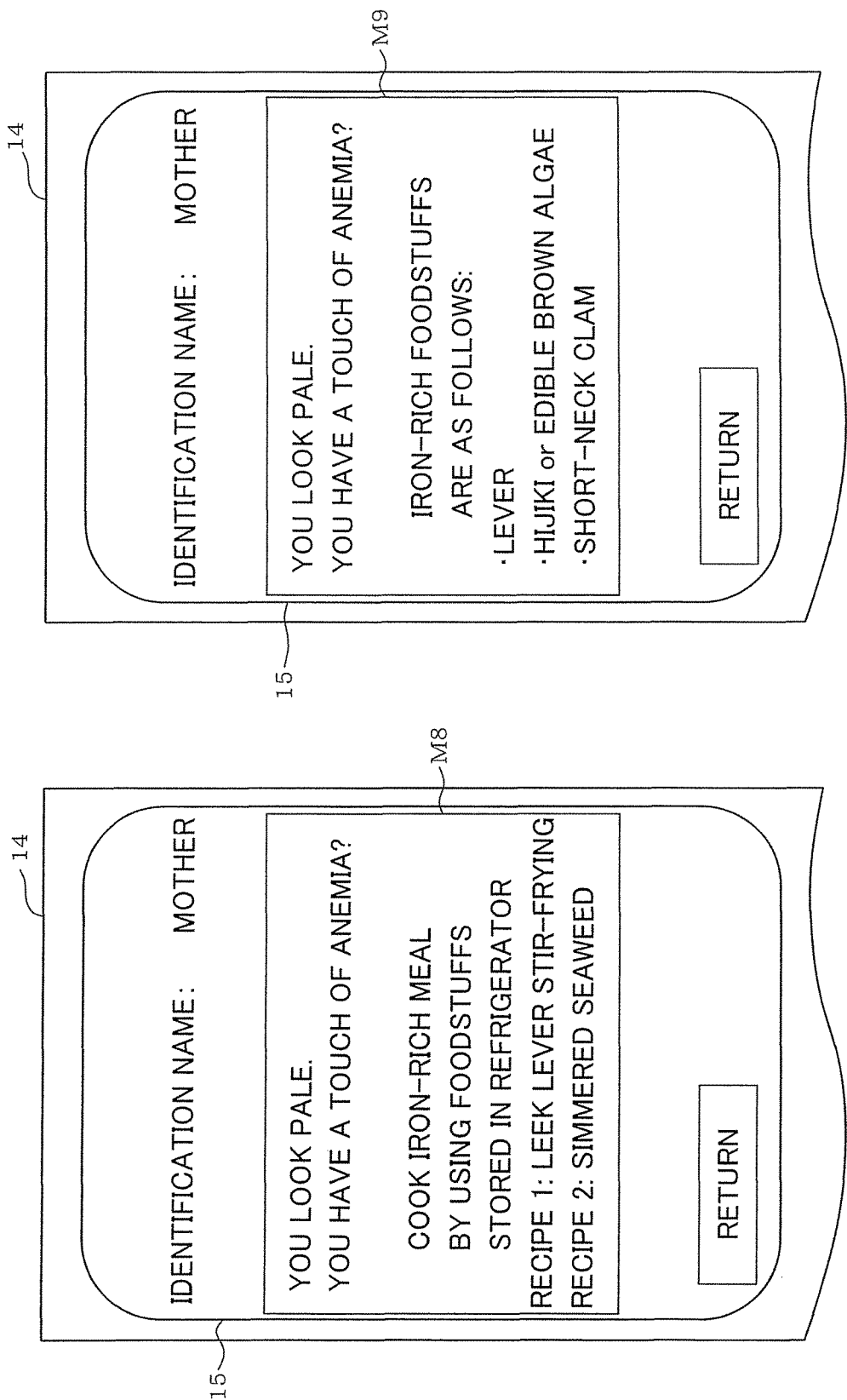

REFRIGERATOR WITH ADVICE GENERATING UNIT

CROSS-REFERENCE TO RELATED APPLICATIONS

This application is based upon and claims the benefit of priority from the prior Japanese Patent Application No. 2012-210849 filed on Sep. 25, 2012 and the prior PCT International Application No. PCT/JP2013/73800 filed on Sep. 4, 2013, the entire contents of both of which are incorporated herein by reference.

FIELD

Embodiments herein described relate to a refrigerator having storage compartments for storing foodstuffs.

BACKGROUND

A refrigerator with a function for controlling caloric intake for the purpose of health care has been known. Meanwhile, for health care, it is effective to, not only control caloric intake, but also manage biological information such as a body weight, a blood pressure, and a complexion from which it is possible to estimate the health condition of the person.

However, under current actual conditions, it is difficult to continue to, for example, manage biological information by consciously using measuring instruments such as a weight scale and a blood-pressure gauge, which deteriorate over time.

BRIEF DESCRIPTION OF THE DRAWINGS

FIG. 8 is a first drawing which shows an advice informing mode of Embodiment 1;

FIG. 9 is a second drawing which shows an advice informing mode of Embodiment 1;

DETAILED DESCRIPTION

Figure 1:
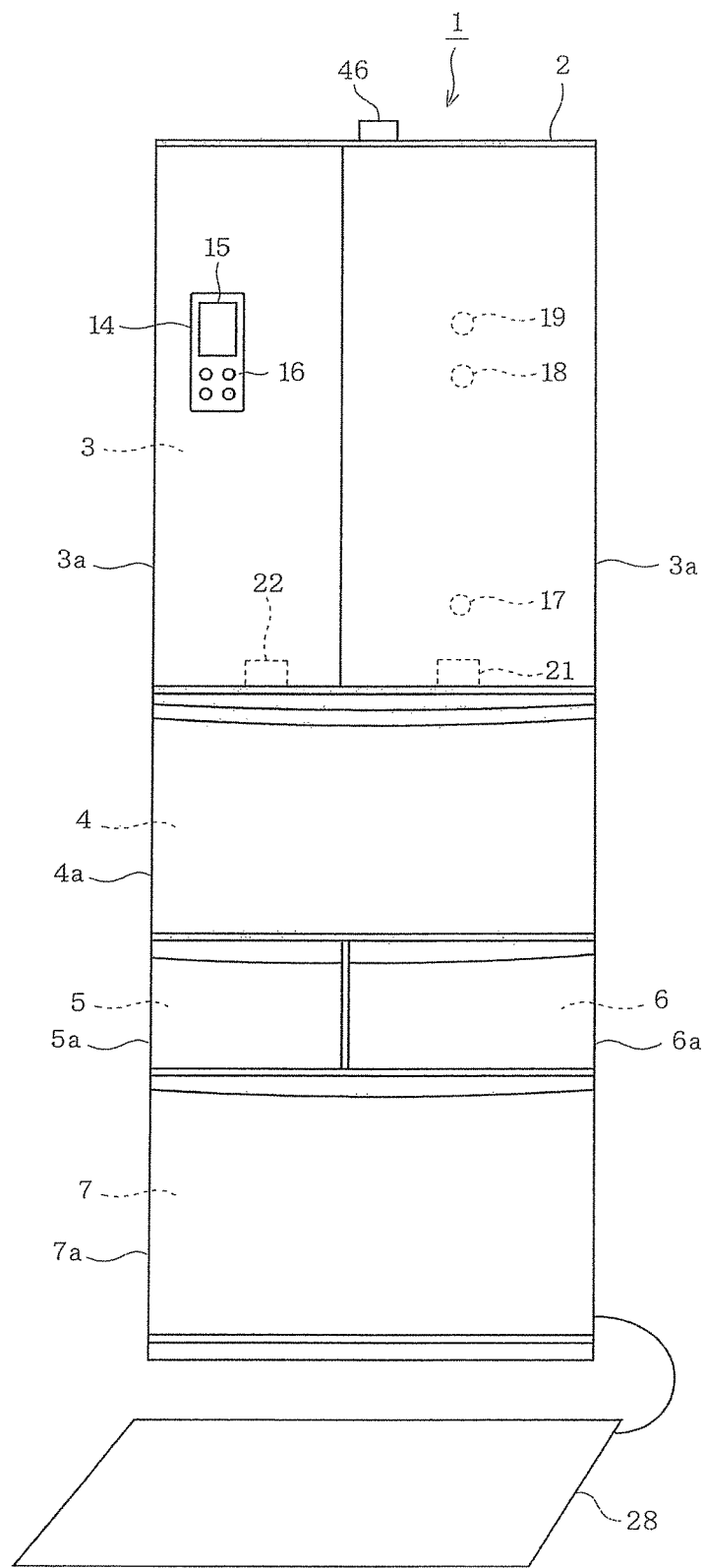
FIG. 1 is a drawing which schematically shows an external appearance of a refrigerator of Embodiment 1.

In general, according to one embodiment, a refrigerator includes biological information obtaining unit for obtaining biological information of a person.

Hereinafter, refrigerators according to a plurality of embodiments will be described with reference to the drawings. In addition, configurations in common with the respective embodiments will be given the same reference numerals, and detailed descriptions thereof will be omitted.

Embodiment 1

A refrigerator of Embodiment 1 will be described with reference to FIGS. 1 to 9.

Figure 2:
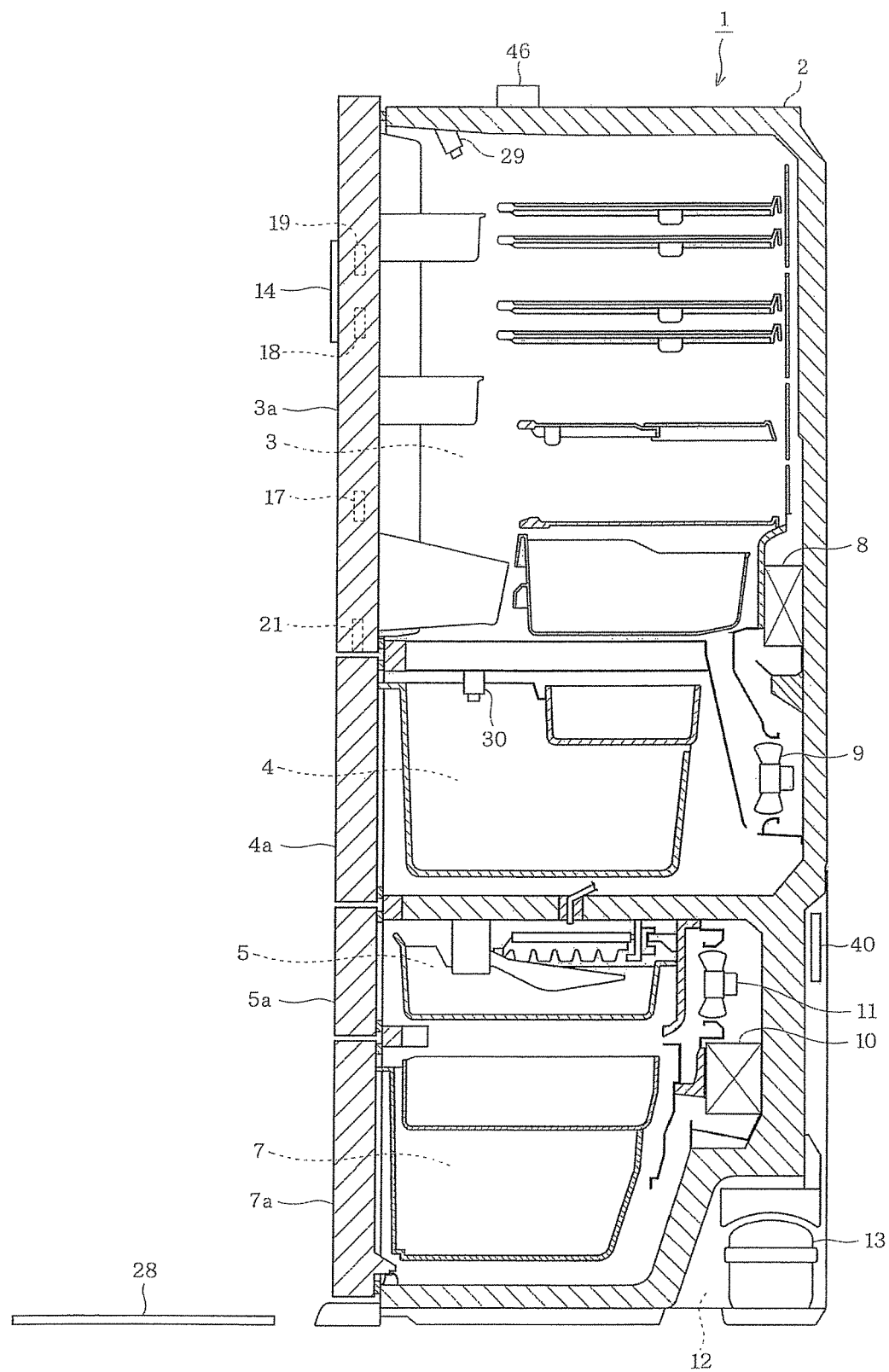
FIG. 2 is a drawing which schematically shows a structure of the refrigerator of Embodiment 1.

As shown in FIGS. 1 and 2, a refrigerating compartment 3 which is a storage compartment for storing foodstuffs, a vegetable compartment 4, an ice-making compartment 5, an upper-stage freezing compartment 6, and a lower-stage freezing compartment 7 are installed, in the order from the top, inside a main body 2 of a refrigerator 1 of Embodiment 1. The refrigerating compartment 3 and the vegetable compartment 4, and the ice-making compartment 5 and the upper-stage freezing compartment 6 are partitioned by insulating partition walls. The refrigerating compartment 3 is configured to, as shown in FIG. 1, open and close respectively on the right and left sides by so-called double doors 3a, and the vegetable compartment 4, and the ice-making compartment 5, the upper-stage freezing compartment 6, and the lower-stage freezing compartment 7 are configured to respectively open and close by drawer type doors 4a, 5a, 6a, and 7a. This refrigerator 1 is installed within a so-called flow line of daily life, which is a place customarily used in a person's daily life (a place to pass through) such as a kitchen.

As shown in FIG. 2, a refrigerating cooler 8 for cooling the refrigerating compartment 3 and the vegetable compartment 4, and a refrigerating fan 9 that circulates the air cooled by the refrigerating cooler 8 are provided in the rear of the refrigerating compartment 3. Further, a freezing cooler 10 for cooling the ice-making compartment 5, the upper-stage freezing compartment 6, and the lower-stage freezing compartment 7 and a freezing fan 11 that circulates the air cooled by the freezing cooler 10 are provided in the rear of the ice-making compartment 5. These refrigerating cooler 8 and the freezing cooler 10 are driven by a compressor 13 disposed in a component chamber 12 in the rear of the lower-stage freezing compartment 7. This compressor 13 composes a well-known freezing cycle along with the refrigerating cooler 8 and the freezing cooler 10. In addition, the configuration of the refrigerator 1 is an example. The respective storage compartments may be different in order of arrangement etc., such that the upper-stage freezing compartment 6 is a switching compartment which is switchable between cold-storage and freezing, or the vegetable compartment 4 is not provided.

As shown in FIG. 1, an operation panel 14 is provided on the left-hand door 3a of the refrigerating compartment 3. This operation panel 14 has a display portion 15 and an operation switch 16. The display portion 15 is composed of, for example, a liquid crystal display, an organic LE display, or the like, and displays a variety of information on the refrigerator 1 with use of text, graphs, and the like. The operation switch 16 is composed of a plurality of switches such as mechanical switches or touch-panel switches, and various types of setting operations with respect to the refrigerator 1 from a person (a resident in a home where the refrigerator 1 is installed in the case of the present embodiment) are input therethrough. In addition, the display portion 15 of the operation panel 14 functions as a informing unit for informing, for example, biological information such as a body weight, a blood pressure, and a complexion from which it is possible to estimate a health condition as will be described later.

A human sensor 17 (composing a human sensing unit), an imaging camera 18 (composing a biological information obtaining unit, an identification unit, and a human sensing unit), and a contactless body temperature sensor 19 (composing a biological information obtaining unit) are provided on the right-hand door 3a of the refrigerating compartment 3. The human sensor 17 has a detector that detects, for example, an infrared ray, a visible radiation, an ultrasonic wave, or the like (or a detector of a combination of detectors therefor), and senses a person located in front of the refrigerator 1. The human sensor 17 may be configured to sense a person in a case of continuously sensing the person for a given time (that is, in the case where the person is sensed several times), or may be configured to be capable of measuring a distance, and sense the person in a case where it is determined that a person is approaching the refrigerator 1.

The imaging camera 18 has an imaging element such as a CCD or a CMOS, and takes a facial image of a person. A facial image is biological information from which it is possible to acquire a variety of information on health conditions such as estimating a blood flow state from a complexion, estimating stress from a facial expression, estimating a change in physical condition or a degree of obesity from a change in shape (a change in facial contour or the presence or absence of swelling), and the like. Further, the imaging camera 18 is used for identifying an individual and measuring a body height of a person by performing image processing of a taken-image. A body height of a person is measured by comparison between a determined position of the imaging camera 18 and a position of a head of the person which is determined by image processing with respect to the position at the time of taking a facial image. Therefore, the imaging camera 18 is configured to change a visual field direction up and down in order to correspond to a certain difference in body height of persons to some extent.

The contactless body temperature sensor 19 detects a body temperature of a person in a contactless manner. In the present embodiment, the contactless body temperature sensor 19 has an infrared detector, and detects a body temperature of a forehead portion of a person serving as an imaging object of the imaging camera 18 as a measuring point. Further, the contactless body temperature sensor 19 is configured to change its measuring point in accordance with the imaging camera 18. In addition, the human sensor 17, the imaging camera 18, and the contactless body temperature sensor 19 are individually provided in the present embodiment. Meanwhile, for example, it may be a configuration in which the human sensor 17 and the contactless body temperature sensor 19 are used in combination, a configuration in which the imaging camera 18 and the human sensor 17 are used in combination, to sense a person from a taken-image, or a configuration in which a so-called infrared camera is adopted, to be used in combination with the contactless body temperature sensor 19. Moreover, it may be a configuration in which it is judged that a person is sensed at the time of carrying out an operation with respect to the operation panel 14.

Figure 3:
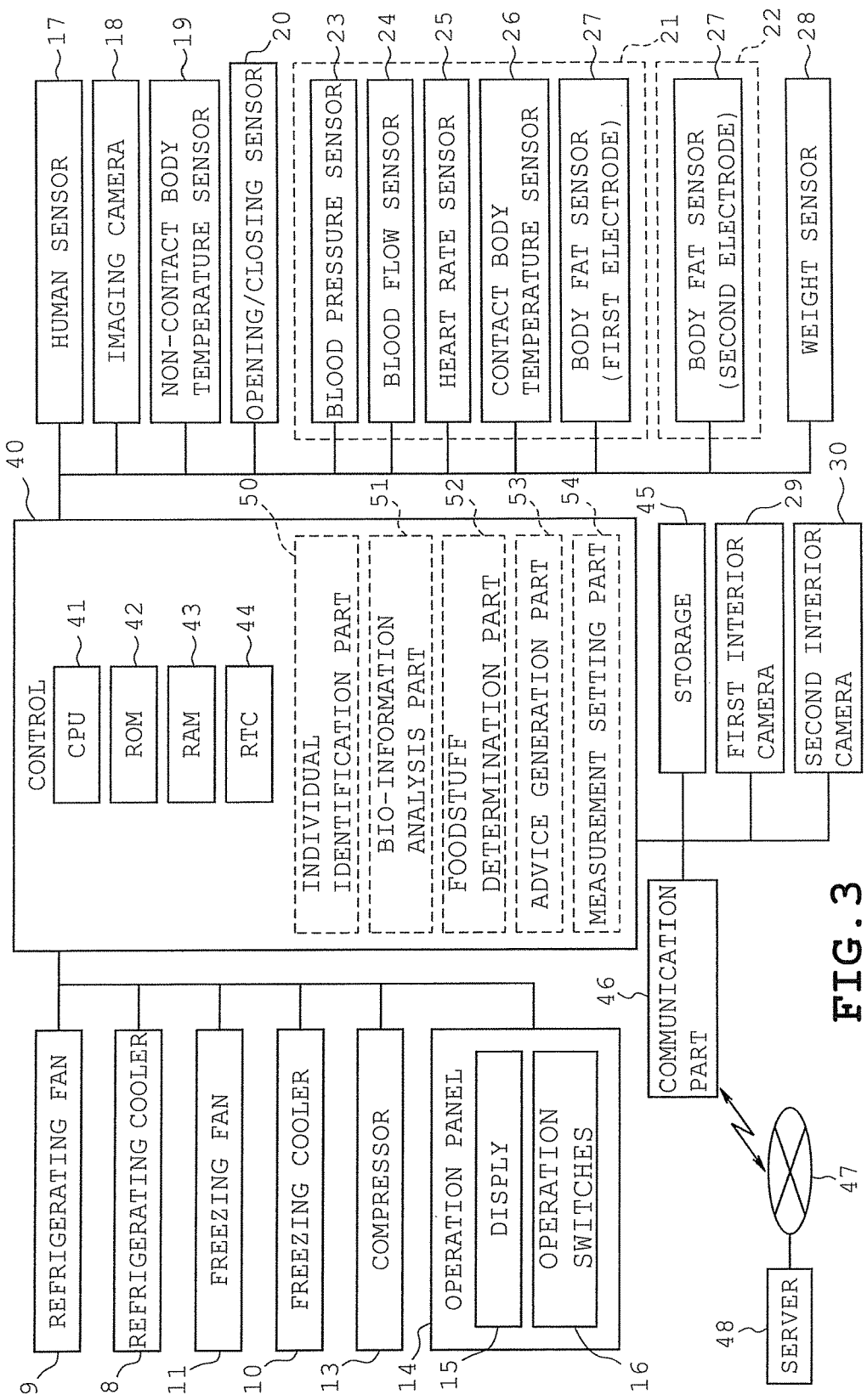
FIG. 3 is a diagram which schematically shows an electrical configuration of the refrigerator of Embodiment 1.

Opening and closing sensors 20 (composing opening and closing operation sensing unit and human sensing unit. Refer to FIG. 3) for sensing whether an opening and closing operation is carried out, are provided at sites on the lower end side of the doors 3a of the refrigerating compartment 3, that is, the sites serving as grips touched by a hand of a person at the time of carrying out an opening and closing operation of the door 3a. Here, a state in which a person is touching the grip of the door 3a in order to open the door 3a is assumed as an "opening and closing operation with respect to the door" in the present embodiment. That is, the opening and closing sensors 20 are capable of sensing that a person touches the door 3a, that is, the person is present in front of the refrigerator 1. That is, the opening and closing sensors 20 function as human sensing unit. These opening and closing sensors 20 are composed of, for example, electrostatic sensors or the like which are provided for the grips.

Further, a compound sensor master unit 21 is provided for the right-hand door 3a of the refrigerating compartment 3, and a compound sensor sub-unit 22 is provided for the left-hand door 3a. Both compound sensor master unit 21 and the compound sensor sub-unit 22 are provided at the sites serving as the grips of the doors 3a. In addition, the positions of the compound sensor master unit 21 and the compound sensor sub-unit 22 are not limited to these, and may be provided for other positions such as the door 4a of the vegetable compartment 4 and the like as long as those are positions which are touched by a person at the time of operating a door. The compound sensor master unit 21 is composed of, as shown in FIG. 3, a blood pressure sensor 23, a blood flow sensor 24, a heart rate sensor 25, a contact-type body temperature sensor 26, and a first electrode of a body fat sensor 27 (all of those compose biological information obtaining unit). This compound sensor master unit 21 is, although not shown, formed into a shape fit into a hand shape of a person, and a shape having a hole portion into which, for example, a middle finger can be inserted at the time of carrying out an opening and closing operation of the door 3a.

When a fingertip is inserted into the hole portion, the blood pressure sensor 23 compresses a blood vessel with a belt (so-called cuff) provided in the hole portion, to thereafter release it, and measures the pressure (cuff pressure) by a sensor provided for the belt, thereby indirectly measure the blood pressure. The blood flow sensor 24 is a blood flow meter of a well-known laser system, ultrasonic system, or infrared system etc., and measures a blood flow in a fingertip. The heart rate sensor 25 measures a so-called electrocardiogram when a fingertip touches the electrode provided for the grip, thereby measuring a heart rate. In addition, it may be a configuration in which the heart rate sensor 25 is used in combination with the infrared system blood flow sensor 24, so as to simultaneously measure a blood flow and a heart rate, or may be a configuration in which not a fingertip, but a palm touching the grip serves as a measuring object.

The contact-type body temperature sensor 26 has a thermistor for example, and measures a temperature of a fingertip touching the grip, thereby measuring a body temperature of the person. In addition, it is a matter of course that the contact-type body temperature sensor 26 may be composed of an infrared detector, to measure a body temperature in a state in which the contact-type body temperature sensor 26 is brought into contact with a fingertip. The body fat sensor 27 has a first electrode on the compound sensor master unit 21 side and a second electrode on the compound sensor sub-unit 22 side, and when a person touches both the first electrode and the second electrode, the body fat sensor 27 flows a weak electric current between the electrodes, to measure a biological impedance, thereby measuring a body fat percentage. A body weight sensor 28 (a so-called weight scale, which composes a biological information obtaining unit) is provided so as to correspond to a floor on the front side of the refrigerator 1, that is, a position at which a person using the refrigerator 1 stands.

Further, as shown in FIGS. 2 and 3, a first refrigerator-interior camera 29 and a second refrigerator-interior camera 30 (both composing foodstuff information obtaining unit) which take images of the inside of the refrigerator are provided in the refrigerator 1. In the present embodiment, the first refrigerator-interior camera 29 takes an image of the inside of the refrigerating compartment 3, and the second refrigerator-interior camera 30 takes an image of the inside of the vegetable compartment 4. Images taken by the first refrigerator-interior camera 29 and the second refrigerator-interior camera 30 are analyzed by a foodstuff discriminant portion 52 (refer to FIG. 3), and are used for obtaining foodstuff information such as types, storage amounts, and the like of stored food products. In addition, the number and the arrangement of cameras, and the storage compartments to be imaging objects are not limited to those shown as an example in FIG. 2. For example, in a case where the vegetable compartment 4 is not provided, a plurality of cameras may be provided in the refrigerating compartment 3 instead of providing the second refrigerator-interior camera 30, a camera for taking an image of the freezing compartment may be provided, or the like, which may be appropriately selected in accordance with a configuration of the refrigerator 1.

The refrigerator 1 having such a configuration is controlled by a control portion 40. The control portion 40 is composed of, as shown in FIG. 3, a computer having a CPU 41, a ROM 42, and a RAM 43, and controls the entire refrigerator 1 in accordance with a computer program memorized in the ROM 42 etc. The control portion 40 has a real-time clock (hereinafter called an RTC 44) serving as a clock unit, and is capable of acquiring clock time information. In addition, as clock time information which can be obtained, a time, date, a day of the week and the like are included.

This control portion 40 is connected to a memory portion 45 and a communication portion 46. The memory portion 45 is composed of, for example, a memory card, an HDD, or the like, and memorizes the biological information obtained (measured) by the biological information obtaining unit described above. This memory portion 45 functions as a memory unit for memorizing biological information and clock time information at which the biological information is measured so as to correspond to one another. The communication portion 46 is for connecting to an external network, and a wireless communication system via a so-called wireless LAN is adopted in the present embodiment. The communication portion 46 connects a so-called Internet 47 corresponding to a network via an unillustrated wireless access point. In addition, the communication portion 46 may be a wire communication system. A server 48 corresponding to an external device is connected to the Internet 47, and the refrigerator 1 performs communication of a variety of information with the server 48 via the communication portion 46. This server 48 is administered by a person or an organization having knowledge for improving biological information, such as a hospital, a personal doctor, or a social welfare service company, a person or an organization which supports or helps to continue to measure biological information continuously, such as a sports gym or an SNS (Social Networking Service).

Further, the control portion 40 has an individual identification portion 50 (composing an individual identification unit), a biological information analysis portion 51 (composing a biological information analysis unit), the foodstuff discriminant portion 52 (composing a foodstuff information obtaining unit), an advice generation portion 53 (composing an advice creating unit), and a measurement setting portion 54. These respective portions are realized using a software by a computer program executed by the CPU 41 in the present embodiment. In addition, it may be a configuration in which these respective portions are realized using a hardware. Further, it may be a configuration in which the control unit for controlling the refrigerator 1 and the control unit for controlling measurements of biological information and communication with the outside are individually provided (for example, a configuration in which a function of measuring biological information is an optional function of the refrigerator 1).

The individual identification portion 50 performs image processing of a facial image taken by the imaging camera 18, and performs so-called face authentication, thereby identifying an individual. In addition, it suffices to adopt a well-known or publicly-known technology for face authentication. However, for example, it may be considered that data of the respective parts such as positions and sizes of eyes, a nose, a mouth, and the like, a facial contour and the like are extracted from a facial image taken, and the extracted data are checked against a data base registered in advance, thereby identifying an individual. For example, information (hereinafter called identification information) to be referred in analyzing/evaluating biological information, such as individual names of "mother" and "father" and their ages, and daily exercise intensities, histories of sports are registered with this data base. This registration of individual information is performed, for example, by input from the operation panel 14.

The biological information analysis portion 51 analyzes the biological information based on the obtained biological information and the registered identification information. In detail, the biological information analysis portion 51 analyzes whether the biological information indicate appropriate values or tendencies for the person in question from, for example, a ratio of the person's body height and body weight (a Body Mass Index or the like), or a rate of change in body weight, a blood pressure, and the like. In addition, the analysis of the biological information may be performed on the server 48 side by a doctor or an instructor referring to the biological information.

The foodstuff discriminant portion 52 acquires foodstuff information based on images of the interiors of the compartments taken by the first refrigerator-interior camera 29 and the second refrigerator-interior camera 30. In detail, the foodstuff discriminant portion 52 extracts names described on foodstuffs from the obtained images, and measures the interior contents of the cases in which the foodstuffs are stored, and the like, thereby acquiring foodstuff information such as the types, the storage amounts, and the like of the foodstuffs. In addition, instead of the cameras, a sensor which measures a weight of foodstuffs, a sensor which senses whether foodstuffs are housed at a predetermined position, and the like may be provided, and foodstuff information may be obtained based on the sensed results of those sensors.

The advice generation portion 53 creates advice for improving the biological information, that is, advice about health care based on the analysis results of the biological information, and with reference to the foodstuff information. In the case where an analysis result of a high blood pressure is obtained, because it is considered favorable to cut down on salt intake, and ingest a proper balance of protein, potassium, magnesium, calcium, and the like in order to reduce a rise in blood pressure, the advice generation portion 53 determines the levels of protein, potassium, magnesium, calcium, and a salt content exercising an effect on blood pressure by coefficients Pt, Kt, Mgt, Cat, and St, and determines a rise-in-blood-pressure suppression effect value based on a calculating formula as the following Formula (1). In addition, because a salt content raises a blood pressure, a salt content is to be subtracted in Formula (1).

$$\begin{aligned}\text{Rise-in-blood-pressure suppression effect value} =\\ \text{(contained amount of protein–standard value of}\\ \text{protein amount)} \times Pt + \text{(contained amount of}\\ \text{potassium–standard value of potassium}\\ \text{amount)} \times Kt + \text{(contained amount of magnesium–}\\ \text{standard value of magnesium amount)} \times Mgt +\\ \text{(contained amount of calcium–standard value of}\\ \text{calcium amount)} \times Cat - \text{(contained amount of}\\ \text{salt–standard value of salt amount)} \times St\end{aligned} \quad (1)$$

Further, in the case where an analysis result that a complexion is poor and the person is likely anemic is obtained, the advice generation portion 53 creates advice about anemia prophylaxis. It is effective to ingest iron for anemia prophylaxis, meanwhile, there are components that help and prevent absorption of iron into a human body. Accordingly, the preventive effect may be reduced depending on foodstuffs in some cases. For example, it is said that vitamin C and protein help in the absorption of iron, meanwhile, tannin impairs absorption of iron. Therefore, the advice generation portion 53 determines coefficients Feh, Vch, Ph, and Th showing the effects on anemia prophylaxis with respect to iron, vitamin C, protein, and tannin, and determines an anemia prophylaxis effect value based on a calculating formula as the following Formula (2).

$$\begin{aligned}\text{Anemia prophylaxis effect value} = \text{contained amount}\\ \text{of iron} \times Feh + \text{contained amount of iron} \times \text{(contained amount of vitamin C–standard value of}\\ \text{vitamin C amount)} \times Vch + \text{contained amount of}\\ \text{iron} \times \text{(contained amount of protein–standard}\\ \text{value of protein amount)} \times Ph - \text{contained amount}\\ \text{of iron} \times \text{(contained amount of tannin–standard}\\ \text{value of tannin amount)} \times Th\end{aligned} \quad (2).$$

Then, the advice generation portion 53 creates, as advice about dietary life, the types and use amounts of foodstuffs with which it is possible to achieve the determined blood pressure suppression effect value and anemia prophylaxis effect value, or a recipe for cooking using those. In addition, with respect to the advice generation portion 53, it is a matter of course that the advice assumed in the present embodiment includes, for example, presentation of information not directly including foodstuffs, such as "Please cut down on salt intake," "Please take iron," "Please remember to exercise because of increasing tendency in body weight," and the like, presentation of foodstuffs themselves such as "Liver is rich in iron," "Tea may inhibit iron intake," and the like, or a recommendation to purchase foodstuffs which are currently not stored, but helpful for improving biological information, such as "Please purchase liver because no liver is stored" as will be described later, and the like. The created advice is displayed on the display portion 15 of the display panel, to be informed to a person.

The measurement setting portion 54 sets conditions for measurements at the time of measuring biological information. For example, in the present embodiment, the compound sensors are composed of the blood pressure sensor 23, the blood flow sensor 24, the heart rate sensor 25, the contact-type body temperature sensor 26, and the body fat percentage sensor 27. However, when the blood pressure sensor 23 always operates, it is assumed that the fingers are tightened each time a door is operated, which may bother the person. Therefore, the measurement setting portion 54 sets conditions for measurements of biological information to be measuring objects.

As the conditions for measurements, for example, it may be conceived of

Setting biological information to be measuring objects by oneself.

Performing measurements of ones such as a facial image or the contactless body temperature sensor 19, which do not interfere with an action of a person for their measurement, and ones such as the contact-type body temperature sensor 26 by which a measured result is immediately obtained, every time.

Performing measurements of ones such as the blood pressure 23 and the body fat rate sensor 27 for which it takes a certain amount of time for their measurement, which may possibly have an effect on the action of a person, based on an instruction by a person. In this case, for example, a measurement switch or the like may be provided for the operation panel 14, and a measurement is started when a person operates the measurement switch.

Setting a clock time for measurement in a specific range or to a specific day of the week according to a life pattern.

Assuming a case where the refrigerator 1 is used several times such as preparing meals, and not performing a measurement or adopting an initial measured result in a case of a short time elapsed from the previous measurement. In addition, the above-described conditions for measurements are just examples, and not limited thereto.

Next, the effects of the refrigerator 1 will be described.

The refrigerator 1 has storage compartments for storing food products as described above, and is therefore used every day while cooking, and is used by a person who frequently stops in front of it during daily life. Further, because a life cycle of a person is repeated in substantially a constant pattern, it is considered that a person may use the refrigerator 1 at almost the same hour every day. Further, for example, in the case where the door of the refrigerator 1 is opened and closed, it is considered that a person may be in substantially the same posture according to the layout of a room where the refrigerator 1 is installed, the opening and closing direction of the door, and the like. That is, it is considered that a person may be, in substantially the same posture at a certain clock time, present in the vicinity of the refrigerator 1. Therefore, the fact that the refrigerator 1 installed within a flow line of daily life is capable of measuring biological information is a motivation for continuously measuring biological information by itself.

Hereinafter, a flow of measuring biological information will be described. In addition, the following processings will be performed by the above-described respective portions. However, for simplifying the explanation, the refrigerator 1 will be principally described. Further, it is assumed that the registration of the above-described identification information and the like has been already carried out, and it is set to measure all the biological information illustrated above by the measurement setting portion 54.

Figure 4:
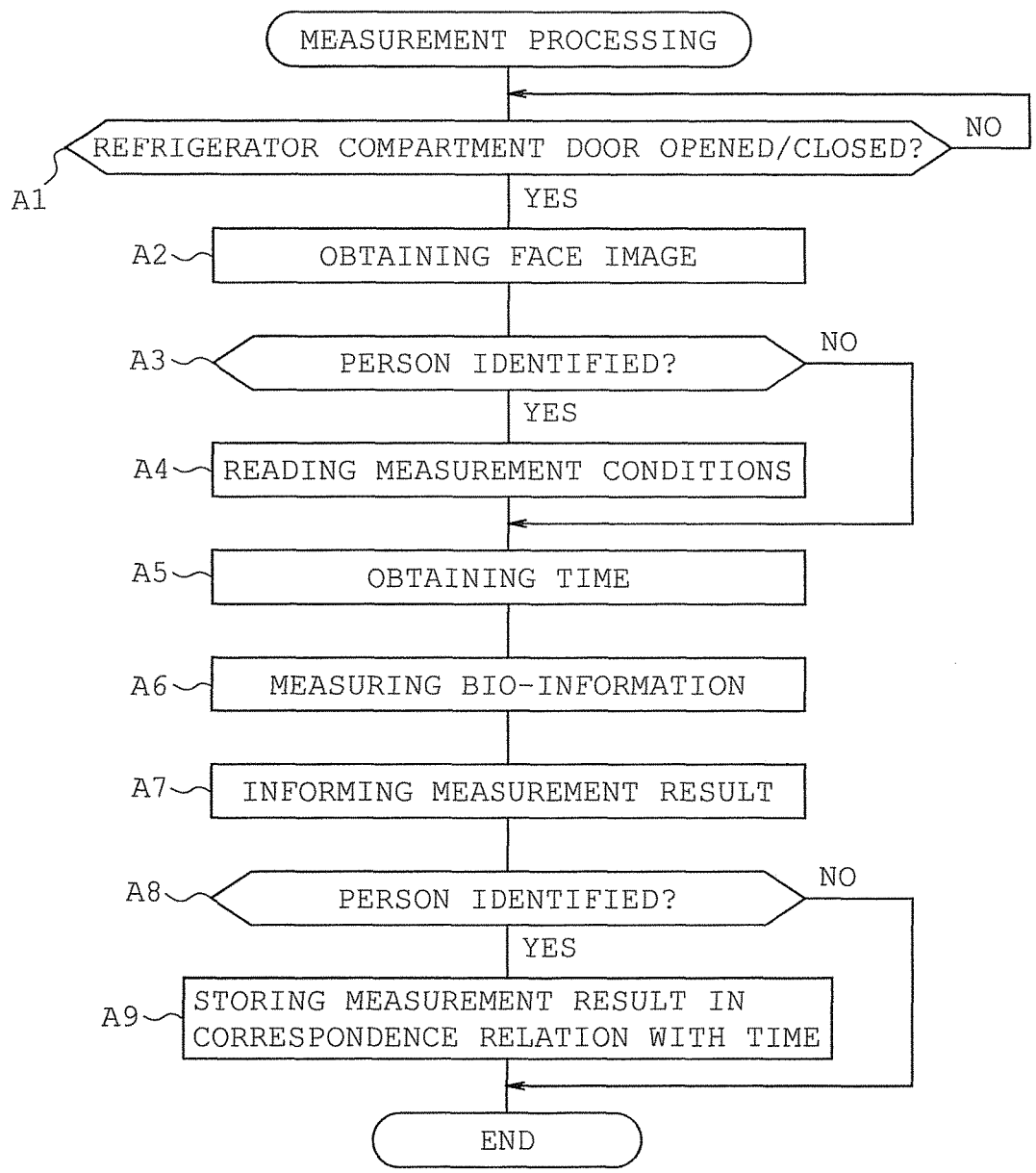
FIG. 4 is a diagram which shows a flow of measurement processing by the refrigerator of Embodiment 1.

The refrigerator 1 executes the measurement processing shown in FIG. 4, and judges whether an opening and closing operation with respect to the door of the refrigerating compartment 3 is carried out (A1). The reason for that the door of the refrigerating compartment 3 serves as a sensing object in the present embodiment is because, in an opening and closing operation with respect to the door of the refrigerating compartment 3, a person is likely situated so as to face substantially the front, that is, the person likely faces toward the imaging camera 18, which makes it possible to take the person's facial image from the front thereof, and a position where the person stands and the person's posture may be substantially the same. That is, the opening and closing sensors 20 function as human sensing unit as well. In addition, because the opening and closing sensor 20 senses that the person is touching the grip as described above, when an opening and closing operation is carried out, the person naturally stands in front of the refrigerator 1.

Next, the refrigerator 1 acquires a facial image of the person (A2). In this Step A2, the obtainment of a facial image is performed in order to acquire biological information such as a complexion and swelling, and in order to identify an individual by face authentication. Therefore, when a facial image is obtained, it is determined whether it is possible to identify an individual by face authentication (A3). At this time, when it is possible to identify an individual (A3: YES), after the conditions for measurements are read out from the memory portion 45 and the like (A4), clock time information is obtained (A5). On the other hand, when it is impossible to identify an individual (A3: NO), the process directly proceeds to step A5. This is because it is possible to measure biological information even when registration thereof has not been completed. Hereinafter, it is assumed that it is possible to identify an individual.

When the clock time information is obtained, the refrigerator 1 measures biological information (A6). In this Step A6, as described above, the measurements of a body temperature, a blood pressure, a blood flow, a heart rate, and a body fat percentage are performed. In addition, a facial image may be obtained again in Step A6. At this time, in a case where it is impossible to perform a measurement of a body fat percentage or the like, which is required to touch a plurality of places (the first electrode and the second electrode), that item may be not measured, or the refrigerator 1 may prompt the person to touch the places by a display or voice.

Figures 5, 6:
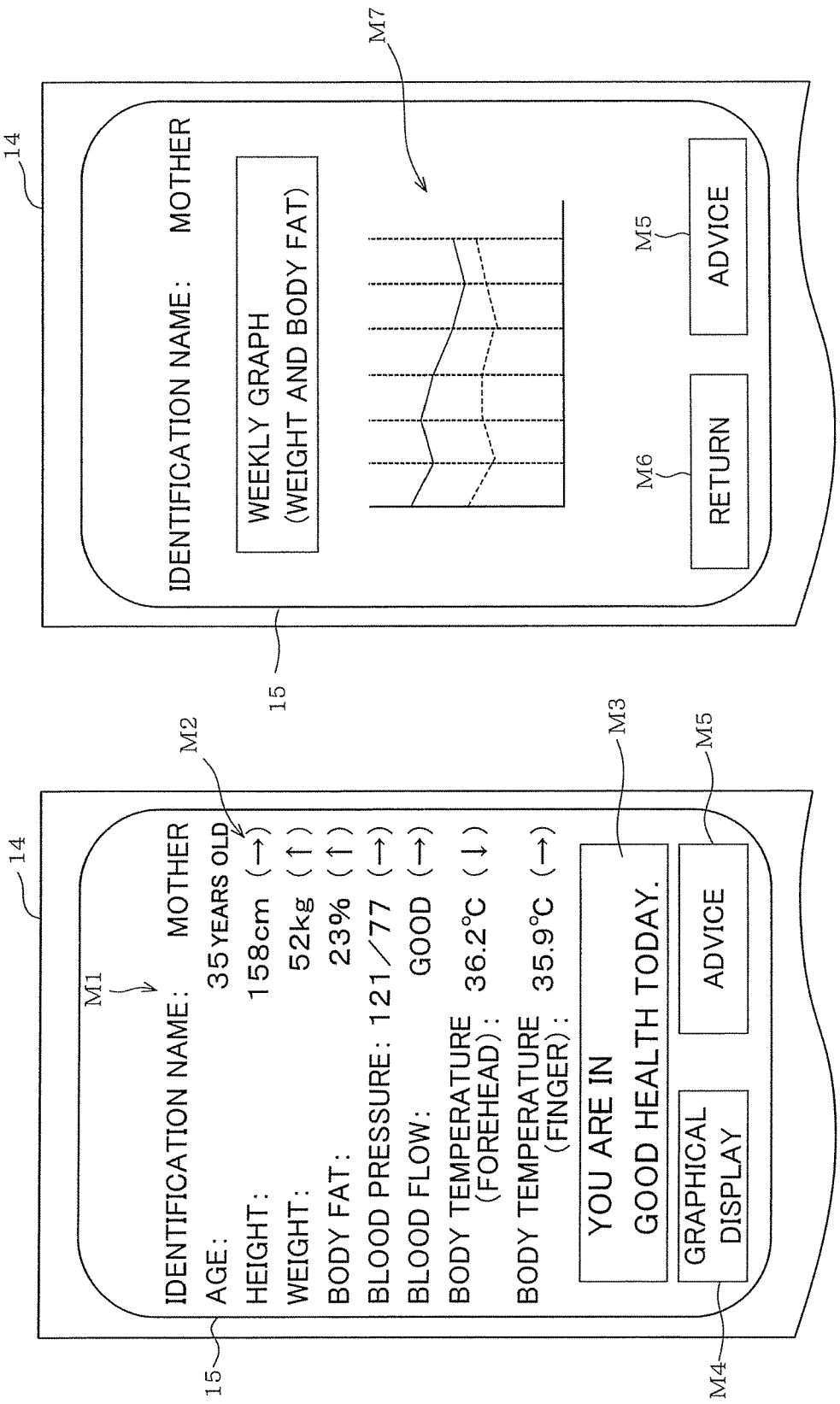
FIG. 5 is a first drawing which shows a biological information informing mode of Embodiment 1.
FIG. 6 is a second drawing which shows a biological information informing mode of Embodiment 1.

When the measurements of the biological information are completed, the refrigerator 1 informs measured results thereof (A7). In detail, the refrigerator 1 informs the measured results by displaying those on the display portion 15 as shown in FIG. 5. In the case of FIG. 5, a result display area M1 indicating the measured results of the identification information such as a name ("mother") and an age, and biological information such as a body height, a body weight, a body fat percentage, a blood pressure, and a body temperature, and a comparison display area M2 indicating analysis results of comparisons with measured results of the day before and the like are provided in the display portion 15. In the comparison display area M2, by way of comparisons with the day before, an up-pointing arrow (↑) indicates a rise in comparison with the day before, a right-pointing arrow (→) indicates no change in comparison with the day before, and a down-pointing arrow (↓) indicates a drop in comparison with the day before. Further, a comment area M3 indicating a comment for an overall health condition based on the analysis results of the biological information ("Good" in the case of FIG. 5) is provided in the display portion 15.

Further, in the case where it is possible to identify an individual as in this case, when a graph display button M4 is operated, as shown in FIG. 6, the result display area M1 is switched to, for example, a history display area M7 on which a weekly history of the biological information is displayed. In addition, the biological information displayed on the history display area M7 is not limited to a body weight and a body fat percentage, and other items such as a basal body temperature change graph, a comparison with a facial image one month ago may be displayed. At this time, items to be displayed may be set by a person. When a return button M6 is operated in a state in which the history display area M7 is displayed, the display is switched to a display mode shown in FIG. 5. In this way, the refrigerator 1 informs the measured biological information in real time.

Next, when an individual has been already identified in Step A3 (A8: YES), the refrigerator 1 memorizes the measured results in the memory portion 45 so as to correspond to the clock time information obtained in Step A5 (A9). Further, when an individual has not yet been identified (A8: NO), the refrigerator 1 terminates the measurement processing directly.

Moreover, the refrigerator 1 is originally to store foodstuffs. Then, among foodstuffs, there are many foodstuffs having an effect on biological information as described above. Then, the refrigerator 1 generates advice for improving biological information and informs it as follows based on foodstuffs stored therein.

Figure 7:
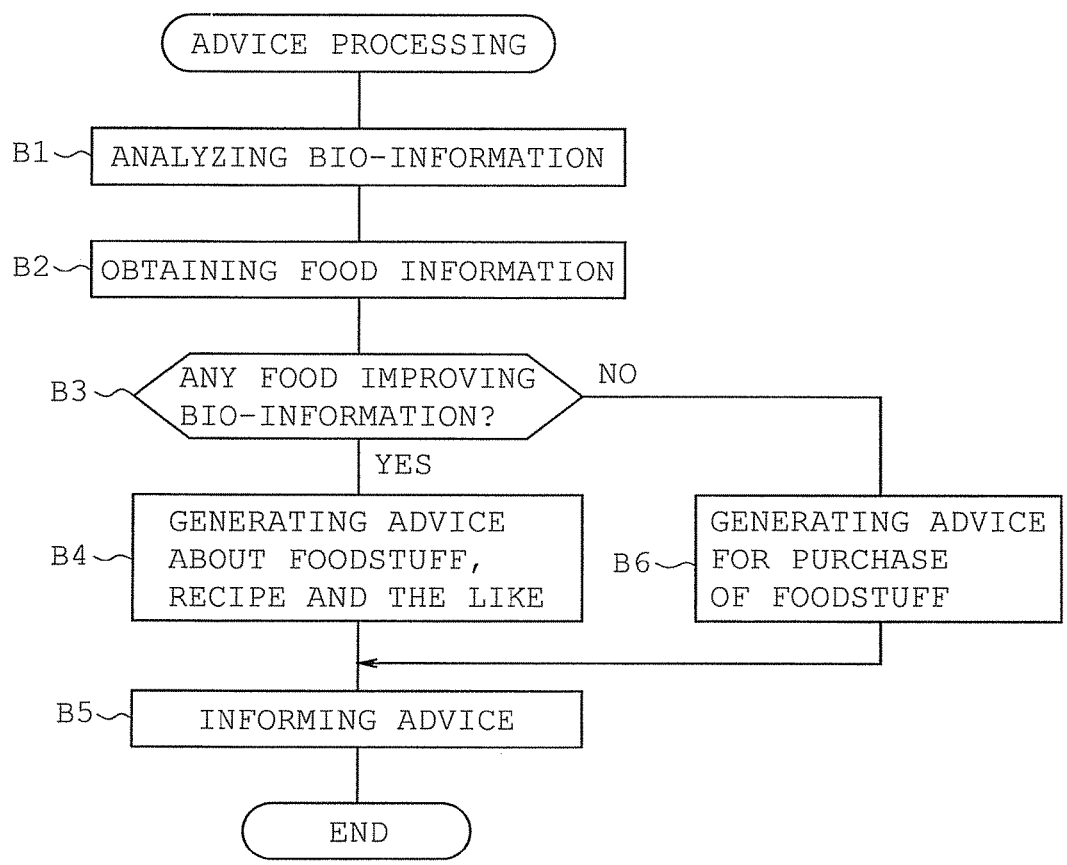
FIG. 7 is a diagram which shows a flow of advice processing by the refrigerator of Embodiment 1.

For example, when an advice button M5 shown in FIG. 5 is operated, the refrigerator 1 executes advice processing shown in FIG. 7, and analyzes the biological information first (B1). In this Step B1, not only the biological information of the day, but also biological information in the past history are analyzed. Next, the refrigerator 1 acquires foodstuff information based on images of the interiors of the compartments taken by the first refrigerator-interior camera 29 and the second refrigerator-interior camera 30 (B2), and determines whether there are foodstuffs with which it is possible to improve the biological information (B3). Then, in the case where there are foodstuffs with which it is possible to improve the biological information (B3: YES), the refrigerator 1 generates advice about foodstuffs or a recipe using the foodstuffs (B4), and informs the advice (B5). For example, the refrigerator 1 recognizes vegetables stored in the vegetable compartment 4 by the second refrigerator-interior camera 30, and generates a recipe using vegetables that are plentiful etc., as advice. Then, as shown in FIG. 8, the refrigerator 1 informs the advice by displaying being likely anemic as an analysis result of the biological information, a message for prompting ingestion of iron in order to improve it, a recipe using the stored foodstuffs, and the like on the advice display area M8.

On the other hand, in the case where there are no foodstuffs for improving the biological information (B3: NO), the refrigerator 1 creates advice about purchase of foodstuffs such as information on foodstuffs contributing to the improvement in the biological information (B6), and informs the advice (B5). In detail, as shown in FIG. 9, the refrigerator 1 informs the advice by displaying liver, hijiki, little clams, and the like as foodstuffs containing iron that are plentiful on the advice display area M8.

In this way, the refrigerator 1 is capable of continuously measuring the biological information by performing measurements of the biological information and informing, to inform advice, thereby contributing to the improvement in the biological information.

The following effects are exerted in accordance with the refrigerator 1 of the present embodiment described above.

The sensors to measure the biological information are provided in the refrigerator 1 which is installed within a flow line of daily life and used every day, thereby causing a person to unconsciously stop in a place at which the biological information is measured, and to necessarily look at it, and therefore, the person never accidentally forgets measurement thereof. Accordingly, it is possible to prompt continuous measurements of biological information so as not to make a person conscious of it, which makes it possible to continuously manage the biological information.

At this time, because a life pattern of a person is substantially constant in many cases, and it is possible to measure the biological information just around the same time, and a posture of the person is substantially the same at the time of utilizing the refrigerator 1, it is possible to measure the biological information under similar conditions, which makes it possible to reduce variations in measurement.

Because the informing unit is provided in the refrigerator 1, it is possible to confirm the measured results immediately after the measurements of the biological information. Further, because it is possible to display the history of the measured biological information, it is possible to effectively recognize a situation of improvement in dietary life of the person himself/herself.

As one of the causes that continuous management of biological information does not last long, the point that managing the measured results for himself/herself is bothersome even though measurements are performed is cited. However, the refrigerator 1 memorizes biological information so as to correspond to clock time information in chronological order. That is, because the measurements and the management of the measured results are performed on the refrigerator 1 side, it is possible to prompt continuous measurements of biological information so as not to bother a person. Then, it is possible to measure not only the biological information of the day, but also the history of past biological information serves as an object of management, thereby it is possible to recognize not only the temporary values of the biological information, but also longer-term changes in biological information (for example, a graph shown in FIG. 6 or the like), which is made more useful for health care. Further, a so-called schedule management function is equipped therein, or the refrigerator 1 is caused to cooperate with an external scheduler, to display a notable event (for example, attending an athletic festival, training, dining out, or the like) along with a graph, thereby it is possible to compare the changes in biological information before and after it, which makes it possible to recognize an influence and an effect of each event.

Because biological information is automatically measured when an opening and closing operation with respect to the door 3a is sensed by the opening and closing sensor 20, it is possible to measure the biological information so as not to make a person conscious of it. At this time, because a motion made by the person in order to measure the biological information is basically a motion for using the refrigerator 1 (standing in front of the refrigerator 1, touching the door 3a with the person's hand), the biological information is automatically measured every time the refrigerator 1 is used, and therefore, it is never forgotten to measure the biological information.

Because the measured results of the biological information are informed, it is made useful for management of physical condition.

Because an individual is identified and biological information is managed individually and in chronological order, it is possible to respond to a case where a plurality of persons use the refrigerator 1. In addition, it is possible to measure a person other than a registered person in the present embodiment. On the other hand, protection control limiting measuring objects, so as not to perform measurements with respect to a person unable to be registered (an unregistered person), or the like may be performed.

Because body temperatures fundamental to health care are measured, to be stored in the memory portion 45 in chronological order, it is possible to perform the body temperature management. Further, although a basal body temperature differs in individuals, an individual is identified, to memorize the person's body temperatures, thereby it is possible to recognize the physical condition of the day from the past changes.

Because a facial image is taken, it is possible to estimate various information on a health condition. Further, because a facial image is also memorized, for example, it is easier to recognize a difference from the current one (that is, whether a person gained weight or lost weight) in comparison with a past facial image, which is therefore a barometer of a health degree at the present moment. Further, when a person feels a gain in weight, the person tries to lose the body weight, that is, useful for improvement in health awareness.

Because a body fat percentage is measured, for example, when a body fat percentage is increased even though a body weight is decreased, it is possible to judge that the person is not quite healthy or the like.

A body weight is a fundamental item for health care, and it is possible to measure the body weight every day, thereby making a person not only care about management of physical condition of that day, but also try to be moderate in the case where the body weight tends to increase, which is made useful for long-term health care. Further, because it is possible to simply and casually perform measurements by merely standing in front of the refrigerator 1, it is possible to quantify short-term changes, for example, the effects due to the diet meal by performing the measurement before and after a diet meal, to recognize those. Further, a body weight, a body fat percentage, and the like are measured to be informed by the refrigerator 1, thereby making a person change foodstuffs used for cooking or an amount of intake thereof, or refrain from a beer when the person thinks of "having a beer" after taking a bath etc., which is useful for improvement in health awareness from a long-term perspective.

Measuring a blood pressure is made useful for health care. Further, because the blood pressure sensor 23 is provided for the grip, a position of a fingertip (sensing site) with respect to a position of a heart is always fixed constant. Therefore, it is possible to perform a stable measurement, that is, a measurement with high accuracy as a long-term comparison object.

A blood flow is measured, and measured results thereof are memorized in chronological order, thereby it is possible to detect a sign that a blood flow has weakened from daily changes, which makes it possible to estimate a vascular illness. This can be achieved by measuring a blood flow continuously over a long term, and memorizing measured results thereof in chronological order. Further, because the blood flow sensor 24 is provided for the grip, it is possible to perform a stable measurement in the same way as blood pressure.

A heart rate is measured, and measured results thereof are measured in chronological order, thereby it is possible to estimate a health condition. Meanwhile, although there may be a variation in heart rate depending on a situation or a state of motion during measurement, by continuing measurements over a long term under substantially the same environment, it is possible to recognize whether a heart rate tends to increase or decrease overall. This can be achieved by measuring continuously those over a long term, and memorizing measured results thereof in chronological order.

It is possible to numerically recognize, for example, a growth state of a child by measuring a body height, and the measurements thereof may be continuously performed in place of a day-by-day growth record.

Because biological information is analyzed, and advice for improving the biological information is created based on analysis results thereof, to be informed, this is motivation for measuring biological information. Further, for example, if a target value for a body weight is set, and advice for reaching the target value is informed, this is further encouragement. At this time, because foodstuff information on foodstuffs stored in the refrigerator 1 are obtained, and advice is created based on the foodstuff information, it is possible to perform health care while making efficient use of the foodstuffs. Moreover, in the case where foodstuffs useful for improving the biological information are not stored, it is advised so as to present the useful foodstuffs, which makes it possible to contribute to health maintenance.

Embodiment 2

A refrigerator according to Embodiment 2 will be described with reference to FIGS. 10 and 11. In addition, because the configuration of the refrigerator is in common with that of Embodiment 1, description thereof will be omitted.

Figure 10:
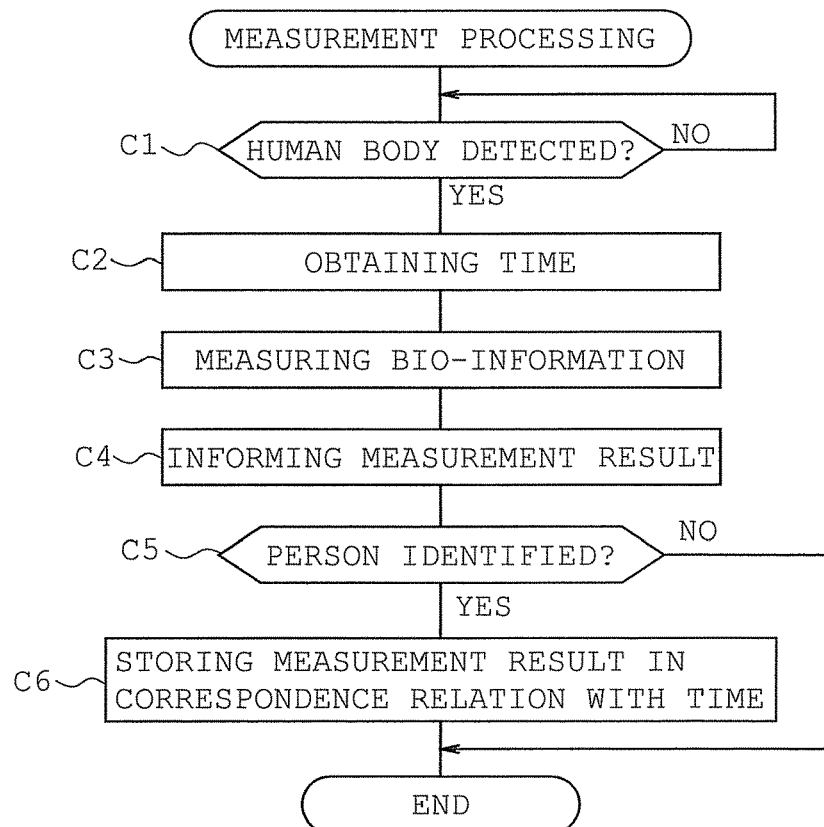
FIG. 10 is a diagram which shows a flow of measurement processing by a refrigerator of Embodiment 2.

The refrigerator 1 judges whether a person is sensed in measurement processing shown in FIG. 10 (C1). At this time, the refrigerator 1 judges whether the person is present in the vicinity of the refrigerator 1. That is, it is sensed that a person touches the refrigerator 1 in Embodiment 1. On the other hand, it is sensed whether a person is present in the vicinity of the refrigerator 1 in Embodiment 2. This is because the contactless body temperature sensor 19 and the imaging camera described above are capable of measuring biological information even when a person does not touch the refrigerator 1, which makes it possible to measure the biological information even when the refrigerator 1 is not used. In addition, it is possible to sense a person by the human sensor 17, the body weight sensor 28, and the like.

When a person is sensed by the refrigerator 1 (C1: YES), in the same way as in Embodiment 1, the refrigerator 1 acquires clock time information (C2), measures biological information (C3), and informs measured results thereof (C5). Then, when it is possible to identify an individual from a facial image and the like, the refrigerator 1 memorizes the measured results so as to correspond to the clock time information (C6). On the other hand, when it is impossible to identify an individual (C5: NO), the refrigerator 1 terminates the processing directly.

Figure 11:
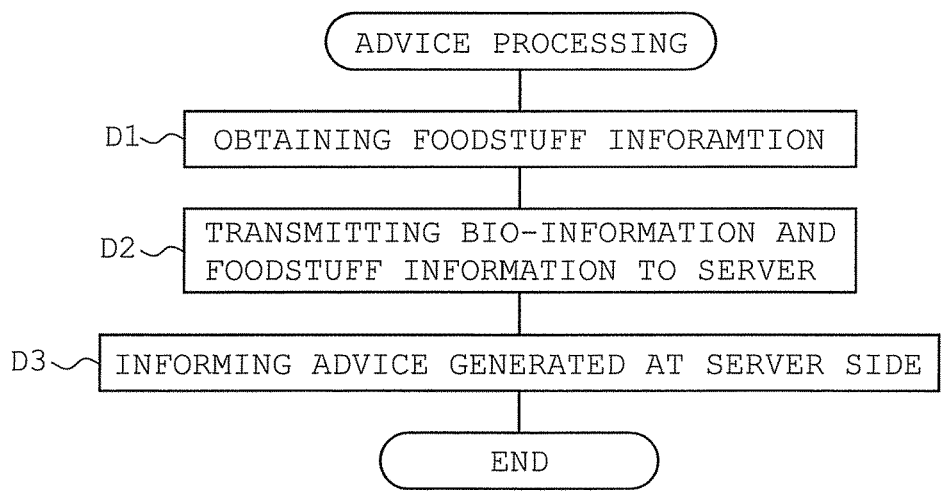
FIG. 11 is a diagram which shows a flow of advice processing by the refrigerator of Embodiment 2.

Next, the refrigerator 1 executes advice processing shown in FIG. 11, and after acquiring foodstuff information (D1), the refrigerator 1 transmits the biological information and the foodstuff information to the server 48 (D2). Then, the refrigerator 1 informs advice created on the server 48 side, as that in FIG. 8 or the like (D3). At this time, on the server 48 side, advice for improving the biological information is created by a third party such as a doctor or an advisor, or the server 48 itself. In addition, the advice processing may be performed even when it is impossible to identify an individual. That is, in the present embodiment, an advice creating unit is configured on the external server 48 side.

In this way, the refrigerator 1 is capable of transmitting the measured biological information to the server 48 side, and is capable of informing advice created on the server 48 side.

This refrigerator 1 naturally exerts the effects described in Embodiment 1, and the refrigerator 1 transmits biological information to the server 48 side in consideration of a case where a situation to be handled is restricted such that there are limitations to memorable information, thereby the refrigerator 1 is capable of performing more appropriate judgment. Further, for example, analysis/judgment of the biological information is performed by a third party such as a doctor having expert knowledge, and advice from the third party is given, thereby it is possible to respond to various situations, and it is possible to inform more appropriate advice.

In this case, taking into consideration that the refrigerator is used over a long period of term in the home, it is possible to sequentially adopt the latest analytic technique for biological information by making the refrigerator connectable to a server, and it is possible to perform health care support effectively using external information, such as prevention of disease, specific countermeasures for health care (exercise prescription, diet treatment, and the like), and proposal of a new recipe for health care, from the biological information. Further, information-sharing with other people is enabled, thereby it is possible to recognize a health condition of a family member who is away from home, or watch for a health condition of a so-called single-living older person from a remote location.

Because a measurement is started when a person is sensed in Embodiment 2, it is possible to measure biological information by merely passing by the refrigerator 1 installed within a flow line of daily life even when the refrigerator 1 is not used. Accordingly, the number of measurements is increased, that is, the number of samples to be comparison objects is increased, thereby it is possible to obtain more detailed and more appropriate measured results, and it is possible to inform more appropriate advice.

Other Embodiments

The examples in which the various types of sensors (biological information obtaining unit) are provided for the main body 2 of the refrigerator 1 are shown in the respective embodiments. However, it may be a configuration in which an external sensor is provided in the vicinity of the refrigerator 1. This is because, as described above, it is possible to prompt continuous obtainment of biological information even when there is a sensor close to the refrigerator 1 used every day.

Types of biological information are not limited to those shown as examples in the respective embodiments. That is, other biological information which are not illustrated may be acquirable.

It may be a configuration in which an external memory unit is provided on the server 48 side, and measured biological information is stored on the server 48 side. In that case, it is possible to respond to a situation in which the capacity of the memory portion 45 becomes short, and the memory portion 45 on the refrigerator 1 side may be omitted, therefore, it is possible to achieve low power consumption and low cost.

The informing unit is provided for the refrigerator 1. However, an informing unit may be provided for an external device, to perform informing on the external device side. In detail, a biological information obtainment system in which the refrigerator 1 and an external device are connected via communication, measurements of biological information are performed by the refrigerator 1, and measured results thereof are informed on the external device side, may be established. In this case, the external device is not limited to that shown in the present embodiment, a so-called personal computer, a mobile communication terminal, or the like which is connected communicatively with the refrigerator 1 via a wireless system or a wired system in a house, may be adopted as an external device. That is, from the viewpoint of a person, the biological information unconsciously measured by the refrigerator 1 is automatically memorized in an external device, a personal computer, or the like, which further improves the convenience. Further, biological information is to be obtained purposefully such that measured results are compared in combination with biological information measured by another biological information obtaining unit not provided for the refrigerator 1, more technical analyses are performed by spreadsheet software or dedicated software of a personal computer, or it is possible to easily share biological information on a so-called diet blog or the like, which becomes motivation for continuing to acquire biological information. Accordingly, it is possible to further contribute to the purpose for health maintenance.

Further, informing is enabled on the external device side, thereby it is possible to perform early response. That is, in a case of "reference" to biological information by the external device shown in the embodiment, it is possible to see the biological information at the time of devising some sort of action on the external device side, meanwhile, it is impossible to refer to the biological information when no action is made on the external device side. On the other hand, when "informing" is performed with respect to the external device side, it is possible to let the external device side know the biological information even when no action is made on the external device side. In this case, it is recommended that informing is performed in combination with the biological information. For example, at the time of forecasting that emergency, response is required even when an identical person who performed measurements does not become conscious of an abnormality in a case where an abnormal value is shown as a blood pressure of a person who is likely hypertensive, "reference" is not waited for passively, but "informing" is actively performed, thereby it is possible to perform a quicker response. Further, when it is set to perform informing to, for example, a cellular phone or the like of a family member, biological information is periodically informed, which therefore makes it possible to watch for a health condition such as "fine today" of a person to be an object from a remote location.

The foodstuff discriminant portion 52 is not limited to the configuration shown in the respective embodiments, and may be another configuration in which a wireless tag is added to a food product, and a type and a storage amount thereof are sensed.

In the respective embodiments, the example in which the compound sensors are composed of the blood pressure sensor 23, the blood flow sensor 24, the heart rate sensor 25, the contact-type body temperature sensor 26, and the body fat percentage sensor 27, and the operation thereof is controlled by setting, is shown. On the other hand, it may be a configuration in which one such as the contact-type body temperature sensor 26 by which a measured result is obtained immediately when a hand touches it, and ones such as the blood pressure sensor 23 and the body fat percentage sensor 27 by which it takes a certain amount of time to obtain a measured result are separately configured, and those start operating by a person's will, that is, when the will to use the blood pressure sensor 23, the body fat percentage sensor 27, and the like is expressed. For example, it may be considered that a measurement of a body fat percentage is performed when a person inputs an operation for measuring biological information to the operation panel 14.

The display 15 of the operation panel 14 is adopted as an informing unit. On the other hand, it may be a configuration in which a dedicated display is provided.

In the respective embodiments, the example in which the opening and closing sensors 20 are independently provided is shown. On the other hand, the biological information obtaining portion may be used in combination with the opening and closing sensors 20, so as to sense an opening and closing operation at the time of touching the contact-type biological information obtaining portion.

In the respective embodiments, the example in which the opening and closing sensor 20 senses that a person touches the grip is shown. On the other hand, it may be a configuration in which an opening and closing state of the door is sensed, for example, it is sensed that the door becomes an open state or a closed state. For example, in the case where the refrigerating compartment 3 is opened and closed by the double doors 3a and the imaging camera 18 is provided for the right-hand door 3a as in the respective embodiments, when it is sensed that the left-hand door 3a is opened, a facial image is taken directly, and when it is sensed that the right-hand door 3a is opened, it is waited until the right-hand door 3a is closed, and a facial image is taken when it is sensed that the right-hand door 3a is closed, thereby it is possible to prevent the facial image from being distorted by taking a facial image while the door 3a is opened.

In the respective embodiments, the example in which the imaging camera 18 is configured to change a visual field direction up and down is shown. However, a wide-angle lens may be provided, so as to expand a visual field, or a plurality of cameras may be provided, so as to correspond to a difference in body height between an adult and a child for example. Further, a visual field direction of the imaging camera 18 may change to right and left. This is because, in some cases, a person may stand, not directly in front of the door 3a, but on the opening side of the door 3a at the time of opening the door 3a of the refrigerating compartment 3. In addition, a visual field of the imaging camera 18 may be directed toward the opening side of the door 3a. This is in the same way as a measuring point of the contactless body temperature sensor.

A half mirror may be provided on the front face of the imaging camera 18, so as for a person to take a facial image at an appropriate position while seeing the person's own facial image. Further, it may be a configuration in which a person is sensed by the imaging camera 18, that is, a configuration in which the imaging camera 18 is used as a human sensing unit.

The imaging camera 18 may be provided in the interior of the refrigerator, so as to take a facial image of a person when the door is opened. In accordance with such a configuration, it is possible to take a facial image in a state in which it is illuminated by a light source such as an illumination in the interior of the refrigerator, that is, in a state in which a face of a person is illuminated at uniform brightness, and it is possible to reduce variation at the time of estimating a physical condition or the like from the facial image.

In the respective embodiments, basically a body fat percentage of an upper body is measured. However, a body fat sensor may be provided on the body weight sensor 28 side, so as to measure a body fat percentage of an entire body.

In the respective embodiments, an individual is identified by a facial image. On the other hand, it may be a configuration in which an individual is identified by any method such as fingerprint authentication, voiceprint authentication, voice authentication with a keyword, pupil authentication, or authentication by selecting registered information or inputting a password.

The measurements of biological information are started based on touching by a person in Embodiment 1, and the measurements of biological information are started when a person is present in the vicinity of the refrigerator 1 in Embodiment 2. On the other hand, in combination of those, biological information may be measured by a contactless system sensor when a person is present in the vicinity, and in the case where the refrigerator 1 is touched to be used thereafter, biological information may be measured by a contact system sensor.

The measurements of biological information are started when a person is sensed in Embodiment 2. On the other hand, a message or the like for prompting the measurements of biological information may be output on a display or with voice when a person is sensed. Thereby it is expected that the measurements of biological information are proactively to be performed.

The display portion 15 is shown as an informing unit. On the other hand, it may be a configuration in which a voice output unit for informing measured results of biological information or advice with voice may be provided, so as to inform those with voice.

In accordance with the refrigerator according to the embodiments, a biological information obtaining unit for acquiring biological information is included. The refrigerator is for storing foodstuffs, and therefore used every day, and is installed within a flow line of daily life in general. By providing the biological information obtaining unit for the refrigerator, it is possible for a person to measure biological information at a place where the person stops every day without having to move to a place where a weight scale is placed in order to measure biological information. Accordingly, it is possible to prompt continuous measurements of biological information so as not to make a person conscious of it, which makes it possible to continuously manage the biological information.

The embodiments of the present invention have been described. However, these embodiments are provided just as examples, and shall not be intended to limit the scope of the invention. These novel embodiments may be implemented as other various modes, and may be subjected to a wide variety of omissions, replacements, and modifications within the range which does not deviate from the gist of the invention. These embodiments and modifications thereof shall be included into the scope of the present invention and the gist thereof, and also included in the inventions described in the Claims of the present invention and equivalents thereof.

EXPLANATION OF REFERENCE NUMERALS

In the drawings, 1 denotes a refrigerator, 3 denotes a refrigerating compartment (storage compartment), 4 denotes a vegetable compartment (storage compartment), 5 denotes an ice-making compartment (storage compartment), 6 denotes an upper-stage freezing compartment (storage compartment), 7 denotes a lower-stage freezing compartment (storage compartment), 15 denotes a display portion (informing unit), 17 denotes a human sensor (human sensing unit), 18 denotes an imaging camera (human sensing unit, biological information obtaining unit, identification unit), 19 denotes a contactless body temperature sensor (biological information obtaining unit), 20 denotes an opening and closing sensor (human sensing unit, opening and closing operation sensing unit), 21 denotes compound sensor master unit (biological information obtaining unit), 22 denotes a compound sensor sub-unit (biological information obtaining unit), 23 denotes a blood pressure sensor (biological information obtaining unit), 24 denotes a blood flow sensor (biological information obtaining unit), 25 denotes a heart rate sensor (biological information obtaining unit), 26 denotes a contact-type body temperature sensor (biological information obtaining unit), 27 denotes a body fat percentage sensor (biological information obtaining unit), 28 denotes a body weight sensor (biological information obtaining unit), 29 denotes a first refrigerator-interior camera (foodstuff information obtaining unit), 30 denotes a second refrigerator-interior camera (foodstuff information obtaining unit), 45 denotes a memory portion (memory unit), 46 denotes a communication portion (communication unit), 47 denotes an Internet (network), 48 denotes a server (external device, external memory unit, informing unit, advice generating unit), 50 denotes an individual identification portion (identification unit), 51 denotes a biological information analysis portion (biological information analysis unit), 52 denotes an foodstuff discriminant portion (foodstuff information obtaining unit), and 53 denotes an advice generation portion (advice generating unit).

The invention claimed is:

1. A refrigerator comprising:
   at least one storage compartment for storing foodstuffs;
   a first sensor configured to obtain biological information of a person automatically upon detection of the person in the vicinity of the refrigerator;
   a memory, coupled to the first sensor to store the biological information automatically upon detection of the person in the vicinity of the refrigerator;
   a second sensor configured to determine the presence of foodstuffs in the storage compartment;
   a biological information analysis portion of a computer configured to analyze the biological information and to obtain foodstuff information comprising information on foodstuffs stored in the storage compartment with which it is possible to improve the biological information;
   an advice generating portion of the computer configured to generate advice for improving the biological information based on the analysis result of the biological information analysis unit, the advice including:
      advice regarding foodstuffs pertinent directly to nutrients and advice relevant to nutrients and not regarding foodstuffs,
      advice about dietary life based on the foodstuff information obtained by the second sensor generated in response to the foodstuffs being detected in the storage compartment, and
      advice about purchase of the foodstuffs generated in response to the foodstuffs not being detected in the storage compartment;
   an input device configured to receive a user request for the advice; and
   a display configured to:
      report a measured result of the biological information, and
      only in response to the user request for advise being received by the input device, report the advice for improving the biological information after reporting the measured result of the biological information.

2. The refrigerator according to claim 1, wherein the memory stores the biological information obtained by the first sensor and corresponding clock time information at which the biological information is obtained.

3. The refrigerator according to claim 1, further comprising an opening and closing sensor configured to sense an opening and closing operation to open or close doors of the storage compartments, wherein the first sensor is configured to obtain the biological information in response to the opening and closing operation being sensed by the opening and closing sensor.

4. The refrigerator according to claim 1, further comprising a third sensor configured to sense the person, wherein the first sensor is configured to obtain the biological information in response to the person being sensed by the third sensor.

5. The refrigerator according to claim 1, wherein the first sensor is configured to obtain a body temperature of the person as the biological information.

6. The refrigerator according to claim 1, wherein the first sensor is configured to obtain a facial image of the person as the biological information.

7. The refrigerator according to claim 1, wherein the first sensor is configured to obtain a body fat percentage of the person as the biological information.

8. The refrigerator according to claim 1, wherein the first sensor is configured to obtain a body weight of the person as the biological information.

9. The refrigerator according to claim 1, wherein the first sensor is configured to obtain a blood pressure of the person as the biological information.

10. The refrigerator according to claim 1, wherein the first sensor is configured to obtain a blood flow state of the person as the biological information.

11. The refrigerator according to claim 1, wherein the first sensor is configured to obtain a heart rate of the person as the biological information.

12. The refrigerator according to claim 1, wherein the first sensor is configured to obtain a body height of the person as the biological information.

13. The refrigerator according to claim 1, further comprising an identification portion of the computer configured to identify the person, wherein the first sensor is configured to obtain the biological information and classify the biological information according to each person identified by the identification portion of the computer.

14. The refrigerator according to claim 1, further comprising a transceiver configured to perform communication with an external device via a network to send the biological information to the external device.

15. The refrigerator according to claim 14, wherein the display is configured to report advice for improving the biological information generated by the external device in response to receiving the biological information.

16. The refrigerator according to claim 14, wherein the biological information obtained by the first sensor is stored along with click time information indicating when the biological information is received by the external device.

* * * * *